United States Patent [19]

Sears

[11] 4,097,502
[45] Jun. 27, 1978

[54] PHOSPHATIDYL SULFONIUM HYDROXIDE COMPOUNDS

[76] Inventor: Barry D. Sears, 43 Bay State Rd., Marblehead, Mass. 02215

[21] Appl. No.: 770,407

[22] Filed: Feb. 22, 1977

Related U.S. Application Data

[63] Continuation-in-part of Ser. No. 731,132, Oct. 12, 1976.

[51] Int. Cl.² .............................................. C08H 3/00
[52] U.S. Cl. .................................. 260/399; 260/403; 260/948
[58] Field of Search ................ 260/399, 403, 947, 948

[56] References Cited

U.S. PATENT DOCUMENTS 3,577,446   5/1971   Rakhit .................................. 260/403

OTHER PUBLICATIONS

Anjea et al., Biochem. Biophys. Acta., 248, pp. 455–457, (1971).
Sears, B. et al., Biochem. Biophys. Res. Comm., 60, pp. 1141–1147, (1974).
Chandra, J., Chem. Phys. Lipids, 4, pp. 104–108, (1970).
Dawson, R., Biochem. J., 102, p. 76, (1967).

*Primary Examiner*—Winston A. Douglas
*Assistant Examiner*—John F. Niebling
*Attorney, Agent, or Firm*—Richard P. Crowley

[57] ABSTRACT

Novel synthetic phosphatidyl sulfonium hydroxide compounds are prepared which have a hydrophobic/hydrophilic balance different from the natural phosphatidylcholine, which alterations are carried out by changes in the sulfonium polar group to provide different surfactant properties.

10 Claims, No Drawings

PHOSPHATIDYL SULFONIUM HYDROXIDE COMPOUNDS

REFERENCE TO PRIOR APPLICATION

This application is a continuation-in-part of application Ser. No. 731,132, filed Oct. 12, 1976.

BACKGROUND OF THE INVENTION

This invention relates to novel chemical compounds structurally related to phosphatidylcholine, to a method of preparing such compounds, and to the use as surfactants of such chemical compounds with or for compounds which have limited or no solubility in aqueous solutions.

Phospholipids and phosphatidylcholine in particular are amipathic compounds in that they consist of a hydrophobic and hydrophilic group or region within the same molecule. Compounds with this amipathic property tend to self-associate in aqueous systems to form micelles which have a hydrophobic interior and a hydrophilic exterior. As a result, these compounds act as surfactants and can solubilize other relatively aqueous insoluble compounds which have limited or no solubility in water, and can partition such insoluble compounds into the hydrophobic region of the micelle. The external polar hydrophilic region of the micelle confers water solubility on the micelle complex or group. It has been well known that such nonsoluble biological compounds, such as cholesterol, cholesterol esters and derivatives, triglycerides and other compounds, can be solubilized in phospholipid micelles. However, the extent of solubilizing power of any surfactant is highly dependent on the ratio of hydrophobic-to-hydrophilic balance within the particular molecule.

For example, natural phosphatidylcholine (that is, lecithin is an excellent emulsifying agent for a number of insoluble biological compounds, such as cholesterol, cholesterol esters and triglycerides, and lecithin is widely used in many industrial applications; for example, the food industry. lecithin is a natural surfactant, and, like other such surfactants, its solubilization properties are derived from its amipathic character; that is, the molecule possesses a region of hydrophobic character (the heterogeneous fatty-acid chain) and a region of hydrophilic character (the polar head group - ethyl-N-trimethyl ammonium group). In addition, lecithin is zwitterionic in the pH range of 2-12, because it possesses a positively charged group (the quaternary ammonium group) and a negatively charged group (the phosphate group). This zwitterionic character stabilizes the ionic structure of the lecithin against any pH fluctuations that would tend to flocculate other natural detergents; that is, other phospholipids or bile salts.

The natural-occurring phospholipids are limited in solubilizing properties. For example, it is known that the maximum amount of cholesterol that phosphatidylcholine can solubilize is in a molar ratio of about one to one, while little, it any, cholesterol ester can be solubilized by phosphatidylcholine. Thus, novel phospholipid compounds which have modified solubilized properties (particularly those which solubilize a greater amount of both biological and industrial compounds than is possible with the natural compound or have different solubilized properties) would be most desirable and useful.

SUMMARY OF THE INVENTION

My invention relates to novel, synthetic, phosphatidyl alkyl sulfonium compounds, which are characterized by enhanced or different solubilizing, surfactant and other properties from the heterogeneous, natural-occurring phosphatidylcholine, to the method of preparing such compounds and to the method of using such compounds as surfactants to solubilize and emulsify other compounds, particularly cholesterol and cholesterol-derived compounds and triglyceride compounds.

I have discovered in particular that the solubilizing or surfactant properties of my novel phosphatidyl compounds can be obtained by variation in the separation of the positively charged sulfonium atom and negatively charged phosphate group; that is, by increasing or decreasing the distance between the groups, such as by increasing or decreasing the number of methylene groups between the charged moieties and/or by delocation of the positive charge on and about the sulfonium atom, such as by replacing one or more of the three methyl groups with other groups, such as with other alkyl groups. Thus, by taking advantage of the zwitterionic nature of natural phosphatidylcholine and changing the structure to produce novel compounds, modified and, in some cases, unexpected surfactant properties are obtained, particularly by the alteration and modification of the polar head group (the alkyl sulfonium) and region of the various phosphatidylcholines.

My new compounds are useful and interesting substitutes for lecithin in solubilizing nonaqueous soluble compounds, and in particular such new compounds may be useful in the regression of atherosclerotic lesions and as antiatherosclerotic agents in blood or other biological fluids, and as stabilizing agents and emulsifiers, particularly in food products.

The novel synthetic phosphatidyl alkyl sulfonium compounds of my invention are represented by the formula:

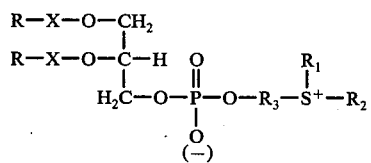

wherein X is an acyl group (C=O), R is a hydrocarbon radical; for example, a long-chain radical, either the same or different or straight or branch chain, and preferably a $C_{14}$–$C_{20}$ fatty acid/alcohol radical; $R_1$ and $R_2$ are hydrocarbon radicals, such as alkyl, alkylene, phenyl or alkyl-substituted phenyl radicals, and preferably are lower alkyl radicals; for example, $C_1$–$C_4$, such as methyl, ethyl, propyl, isopropyl, butyl and isobutyl radicals, phenyl radicals or benzyl radicals, with $R_1$ and $R_2$ being the same or different radicals; and $R_3$ is a hydrocarbon radical, preferably a long-chain hydrocarbon radical of $C_1$–$C_{10}$ carbon atoms, such as alkylene (methylene) radicals, straight or branch-chain. Most preferably, $R_3$ is a $C_2$–$C_5$ methylene chain and has a different number of carbon atoms than $R_1$ and $R_2$. The glycerol backbone of the compound may include the d, 1 or racemic configuration.

Some preferred phosphatidyl alkyl sulfonium hydroxide compounds of my invention are represented by:

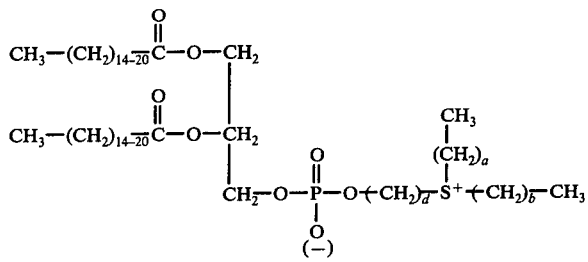

Typical compounds include:

| | | |
|---|---|---|
| I: | a = b = o | d = 2 |
| II: | a = b = o | d = 4 |
| III: | a = b = o | d = 3 |
| IV: | a = b = o | d = 2 |

In my compounds, the R radicals may vary and be composed of natural or synthetic fatty radicals, but preferably are $C_{14}$ to $C_{20}$ fatty and alcohol radicals, or combinations and mixtures thereof. The fatty radicals useful include both saturated and ethylenically unsaturated hydrocarbon radicals, such as those radicals derived from fatty alcohols, such as, for example, myristate, palmitate, oleate, linoleate and sterate radicals and heterogeneous mixtures, such as found in natural products like egg yolk, soybeans and the like. The R and X radicals may be the same or different radicals, but preferably are the same X radicals with the same or different R radicals. In one method of preparation, as hereinafter described, the R radicals will be those radicals of the alkyl sulfonium alcohol selected for the reaction. By the selection of desired fatty radicals and the length thereof, the hydrophobic character of this portion of the synthetic compound may be altered and modified to a desired defined level, such as by selecting the R radical to be the same or different chain length or degree of saturation or substitution.

The polar group or alkyl sulfonium group of my compounds may be composed of substituent radicals to alter te electropositive character of the sulfonium atom, but particularly are $C_1$-$C_4$ alkyl radicals.

My novel compounds would include, but not be limited to:

dioleate phosphatidyl-(isopropyl-S-diethyl) sulfonium hydroxide;
dipalmitate phosphatidyl-(ethyl-S-dimethyl) sulfonium hydroxide;
distearyl phosphatidyl-(ethyl-S-diethyl) sulfonium hydroxide;
oleate-palmitate phosphatidyl-(ethyl-S-dimethyl) sulfonium hydroxide;
dimyristate phosphatidyl-butyl-S-dipropyl) sulfonium hydroxide;
dipalmitate phosphatidyl-(propyl-S-dimethyl) sulfonium hydroxide;
egg phosphatidyl-(propyl-S-dimethyl) sulfonium hydroxide;
soybean phosphatidyl-(propyl-S-dimethyl) sulfonium hydroxide; and mixtures thereof.

My compounds have been described employing derived nomenclature. However, for example, dimyristate phosphatidyl-(butyl-S-dipropyl) sulfonium hydroxide above also may be named as dimyristoyl phosphatidyl-(tetramethylene-S-dipropylmethyl) sulfonium, and the other named compounds may be described similarly.

My compound may be prepared by a variety of methods. However, the preferred method of preparation is to prepare the synthetic phosphatidyl alkyl sulfonium hydroxide by reacting and coupling the polar head group moiety to phosphatidic acid; for example, using triisopropylbenzenesulfonyl chloride in pyridine (see R. Anjea and J. S. Chandra, Biochem. Biophys. Acta 248, 455 (1971) and B. Sears, W. C. Hutton, and T. E. Thompson, Biochem. Biophys. Res. Comm. 60, 1141 (1974)). The phosphatidic acic may be derived from natural or synthetic phosphatidylcholine by the digestion with the enzyme phospholipase D (see R. M. C. Dawson, Biochem J. 102, 76 (1967)). The modified polar head group compound is then synthesized by the general reaction method represented as follows:

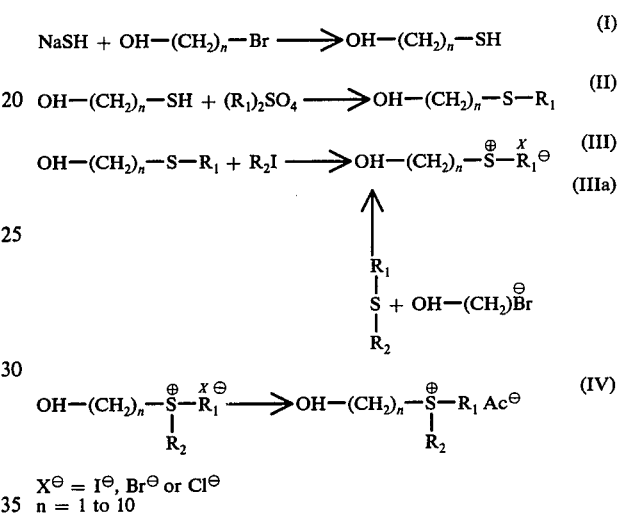

$X^\ominus = I^\ominus, Br^\ominus$ or $Cl^\ominus$
n = 1 to 10

The salt form (for example the Ac acetate form) of the sulfonium salt is obtained by ion-exchanging the sulfonium halide salt (for example the iodide form) in an ion-exchange column equilibrated with the acetate ions. Thus, my method is: to synthesize synthetic phosphatidylcholine or isolate natural phosphatidylchloline; then enzymatically to cleave the phosphatidylcholine to phosphatidic acid; to synthesize a modified hydroxy alkyl sulfonium iodine (III), convert the hydroxy alkyl sulfonium iodine to the corresponding acetate (IV) (the acetate form is more soluble than the halide form in pyridine, the solvent used for coupling) and covalently couple with hydroxyl alkyl sulfonium acetate onto the phosphatidic acid, thereby giving the phospholipid modified in the polar head group. The acetate or weak-acid form may also be used with acetonitrile as the solvent or the iodine form used where the coupling solvent is about a one:one mixture of pyridine and acetonitrile.

My method of preparing synthetic phosphatidyl alkyl sulfonium compounds comprises covalently reacting or coupling in a common nonaqueous solvent typically an organic polar solvent like pyridine or acetonitrile; for example, a nitrogen-containing solvent, the alkyl sulfonium salt preferably the weak salt or halo salt of the alkyl sulfonium compound, which phosphatidic acid and recovering the phosphatidyl alkyl sulfonium hydroxide compound and chromatographically purifying the resulting compound.

My novel synthetic compounds alter and modify hydrophobic-to-hydrophilic-balance properties over those of the natural compounds, such as phosphatidylcholine. Such differences in the hydrophilic-to-hydrophobic balance will effect their surfactant properties.

My invention will be described for the purpose of explanation and illustration only in connection with the preparation of certain preferred compounds. However, it is recognized and is within the scope and intent of my invention and disclosure that other compounds and other methods of preparation can be formulated and used.

DESCRIPTION OF THE EMBODIMENTS

Synthesis of dipalmitoyl phosphatidyl sulfonium hydroxide compunds

Glycerol phosphoryl choline is derived from crude egg yolk phosphatidylcholine using the method of J. S. Chandra, Chem. Phys. Lipids 4 104 (1970). Dipalmitoyl phosphatidylcholine is synthesized according to the method of Cubero Robles, E. and van de Berg, D., Biochem. Biophys, Acta 187 520 (1969). Dipalmitoyl phosphatidic acid is prepared by the enzymatic cleavage of dipalmitoyl phosphatidylcholine by cabbage phospholipase D according to Dawson, R. M. C., Biochem. J. 102 76 (1967). The appropriate hydroxy alkyl sulfonium acetate is covalently linked to the dipalmitoyl phosphatidic acid using 2,4,6 triisopropylbenzenesulfonyl chloride as a coupling agent as described by Sears et al, Biochem. Biophys, Res. Comm. 60 1141 (1974). The phosphatidylcholine analog is then purified by silicic acid chromatography. The detailed synthetic description of the hydroxy alkyl sulfonium compounds and the corresponding phosphatidyl alkyl sulfonium hydroxde compounds are described below.

A. Dipalmitoyl phosphatidyl-(ethyl-S-dimethyl) sulfonium hydroxide (I).

Dimethyl sulfide (.4 moles) and 2-bromo ethanol (0.3 moles) are dissolved in 50 ml of ether and allowed to sit for 24 hours in the dark at room temperature. The precipitated 2-hydroxy ethyl-S-dimethyl sulfonium bromide is filtered and then dissolved in 20 ml of water. The solution is placed on a 2 × 40 cm column of Bio Rad AG1-X8 cation-exchange column in the acetate form. The column is eluted with distilled water. The (2-hydroxy ethyl)S-dimethyl sulfonium acetate is concentrated by dryness. 400 micro moles of the (2-hydroxy ethyl)S-dimethyl sulfonium acetate in methanol is mixed with 300 micro moles of dipalmitoyl phosphatidic acid and then taken to dryness. The mixture is dried under high vacuum against $P_2O_5$ overnight. 700 micro moles of 2,4,6 triisopropylbenzenesulfonyl chloride in 10 ml of dry pyridine is added to the dry mixture. The reaction mixture is stoppered and heated and stirred for 1 hour at 65° C and then stirred for 4 hours at room temperature. At the end of the reaction, the pyridine is evaporated from the reaction. The residue is taken up in 20 ml of chloroform-methanol (2:1) and then 5 ml of distilled water is added. The resulting lower phase is taken to dryness and the residue is taken up in chloroform. The chloroform solution is applied to 2 × 30 cm silicic acid column and the phosphatidyl alkyl sulfonium hydroxide eluted with increasing amounts of methanol in chloroform.

B. Dipalmitoyl phosphatidyl-(butyl-S-dimethyl) sulfonium hydroxide (II).

Dimethyl sulfide (0.4 moles) and 4-bromo butanol (0.3 moles) are dissolved in 50 ml of ether and allowed to sit for 48 hours in the dark at room temperature. The precipitated 4-hydroxy-butyl-S-dimethyl sulfonium bromide is filtered and then dissolved in 20 ml of water. The acetate form of the 4-hydroxy-butyl-S-dimethyl sulfonium cation is prepared as previously described. 400 micro moles of (4-hydroxy butyl)-S-dimethyl sulfonium acetate and 300 micro moles of dipalmitoyl phosphatidic acid are mixed in methanol and taken to dryness. The mixture is dried under high vacuum against $P_2O_5$ overnight. 700 micro moles of 2,4,6 triisopropylbenzenesulfonyl chloride in 10 ml of pyridine is added. The reaction is heated for 1 hour at 65° C and then stirred for 4 hours at room temperature. The reaction is then purified as described above.

C. Dipalmitoyl phosphatidyl-(propyl-S-dimethyl) sulfonium hydroxide (III).

Dimethyl sulfide (.4moles) and 3-bromo propanol (.3 moles) are dissolved in 50 ml of ether and allowed to sit for 48 hours in the dark at room temperature. The precipitated 3-hydroxy-propyl-S-dimethyl sulfonium bromide is filtered and then dissolved in 20 ml of water. The (3-hydroxy propyl)-S-dimethyl sulfonium salt is converted to the acetate salt as previously described. 400 micro moles of (3-hydroxy propyl)-S-dimethyl sulfonium acetate and 300 micro moles of dipalmitoyl phosphatidic acid are mixed in methanol and evaporated to dryness. The residue is dried at high vacuum and against $P_2O_5$ for 12 hours. 700 micro moles of 2,4,6 triisopropylbenzenesulfonyl chloride in 10 ml of pyridine is added. The reaction is heated at 65° C for 1 hour and then stirred for 4 hours at room temperature. The dipalmitoyl phosphatidyl (propyl-S-dimethyl sulfonium hydroxide is purified as previously described.

D. Dipalmitoyl phosphatidyl-(ethyl-S-methyl, ethyl) sulfonium hydroxide (IV).

0.5 moles of 2-mercapto ethanol and 0.7 moles of dimethyl sulfate are dissolved in 100 ml of 25% NaOH and heated for 2 hours at 65° C. The 2-(methyl thio)ethanol is then distilled from the reaction mixture. 0.1 moles of 2-(methyl thio)ethanol is dissolved in 50 ml of ether to which 0.15 moles of ethyl iodine is added. The precipitated 2-hydroxy ethyl S-(methyl,ethyl) sulfonium iodine is removed by filtration and dissolved in 20 ml of water. The (2-hydroxy)-S-methyl, ethyl sulfonium acetate is prepared as previously described. 400 micro moles of (2-hydroxy)-S-ethyl sulfonium acetate and 300 micro moles of dipalmitoyl phosphatidic acid are mixed in methanol and taken to dryness. The residue is dried under high vacuum and against $P_2O_5$ overnight. 700 micro moles of 2,4,6 triisopropylbenzenesulfonyl chloride in 15 ml of pyridine is added to the residue. The mixture is heated for 1 hour at 65° C and then stirred for 4 hours at room temperature. The purification of the dipalmitoyl phosphatidyl-(ethyl-S-diethyl) sulfonium hydroxide is carried out as previously described.

I have described the synthesis of a selected number of preferred phosphatidyl alkyl sulfonium compounds in which the hydrophilic region of the molecule has been chemically modified. As a result, the hydrophobic-to-hydrophilic balance within the molecule is altered. Furthermore, the charge density of the positively charged sulfonium atom is quite different from the positively charged ammonium atom found in lecithin. By changing the hydrophilic region of the phosphatidyl alkyl sulfonium, the hyrophobic-to-hydrophilic balance in each of the phosphatidyl alkyl sulfonium molecules has been altered. These new compounds have utility as solubilizing agents in food-processing, industrial and biological applications. In addition, because of their close structural relation to phosphatidylcholine, they also find application in clinical medicine, such as the regression of atherosclerotic lesions, via the solubilization of deposited cholesterol.

What I claim is:

1. Synthetic phosphatidyl sulfonium compounds represented by the formula:

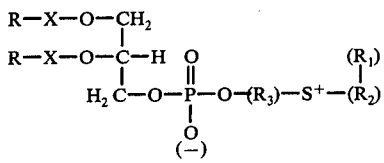

wherein X is an acyl group (C=O); R is a hydrocarbon radical; $R_1$ and $R_2$ are selected from the group of alkyl, alkylene, phenyl and benzyl radicals; and $R_3$ is a methylene radical of from 1 to 10 carbon atoms.

2. The compounds of claim 1 wherein R is a $C_{14}$–$C_{20}$ fatty radical.

3. The compounds of claim 1 wherein $R_1$ and $R_2$ are $C_1$–$C_4$ alkyl radicals.

4. The compounds of claim 1 wherein $R_1$ and $R_2$ are ethyl, propyl, isopropyl, butyl or isobutyl radicals.

5. The compounds of claim 1 wherein $R_3$ is a $C_1$–$C_5$ methylene radical, and R is a $C_{14}$–$C_{20}$ fatty radical.

6. The compounds of claim 1 wherein R is the same radical, and $R_3$ is a different chain length than R and $R_2$.

7. The compounds of claim 1 wherein $R_3$ is a tetramethylene radical and $R_1$ and $R_2$ are methyl radicals.

8. The compounds of claim 1 wherein $R_3$ is a dimethylene radical and $R_1$ and $R_2$ are ethyl radicals.

9. The compounds of claim 1 wherein

is a myristoyl, palmitoyl, oleoyl, linoleoyl, stearoyl, egg yolk or soybean radical.

10. The compounds of claim 1 selected from the group consisting of:

dioleoyl phosphatidyl-(methylethylene-S-diethyl)sulfonium;

dipalmitoyl phosphatidyl-(ethylene-S-dimethyl)sulfonium;

distearoyl phosphatidyl-(ethylene-S-diethyl)sulfonium;

oleoyl-palmitoyl phosphatidyl-(ethylene-S-dimethyl)-sulfonium;

dimyristoyl phosphatidyl-(tetramethylene-S-dipropylmethyl)sulfonium;

dipalmitoyl phosphatidyl-(trimethylene-S-dimethyl)-sulfonium;

egg phosphatidyl-(trimethylene-S-dimethyl)sulfonium;

soybean phosphatidyl-(trimethylene-S-dimethyl)sulfonium; and dipalmitoyl phosphatidyl-(tetramethylene-S-dimethyl)-sulfonium.

* * * * *

UNITED STATES PATENT OFFICE
CERTIFICATE OF CORRECTION

PATENT NO. : 4,097,502
DATED : June 27, 1978
INVENTOR(S) : Barry D. Sears

It is certified that error appears in the above—identified patent and that said Letters Patent are hereby corrected as shown below:

In column 7, claim 1, line 10, in the formula delete "($R_1$)" from being bonded to "($R_2$) in line 11, and insert --($R_1$)-- over "$S^+$" to show bonding thereto.

In column 7, claim 6, line 29, delete "$R_2$" and insert therefor --$R_1$--.

Signed and Sealed this

*Fifth* Day of *December 1978*

[SEAL]

Attest:

RUTH C. MASON
*Attesting Officer*

DONALD W. BANNER
*Commissioner of Patents and Trademarks*